(12) United States Patent
Barthelemy et al.

(10) Patent No.: US 9,533,049 B2
(45) Date of Patent: Jan. 3, 2017

(54) METHOD FOR PREPARING NANOPARTICLES BASED ON FUNCTIONAL AMPHIPHILIC MOLECULES OR MACROMOLECULES, AND THE USE THEREOF

(71) Applicants: UNIVERSITE VICTOR SEGALEN BOURDEAUX 2, Bordeaux (FR); UNIVERSITE DE BOURGOGNE, Dijon (FR); UNIVERSITE DE LA MEDITERRANEE, Marseilles (FR)

(72) Inventors: Philippe Barthelemy, Merignac (FR); Michel Camplo, Marseilles (FR); Nathalie Campins, Valliguières (FR); Bruno Chauffert, Dijon (FR); Florence Bouyer, Chenove (FR)

(73) Assignees: UNIVERSITE D'AIX-MARSEILLE, Marseilles (FR); UNIVERSITE DE BORDEAUX, Bordeaux (FR); UNIVERSITÉ DE BOURGOGNE, Dijon (FR)

( * ) Notice: Subject to any disclaimer, the term of this patent is extended or adjusted under 35 U.S.C. 154(b) by 0 days.

(21) Appl. No.: 14/208,978

(22) Filed: Mar. 13, 2014

(65) Prior Publication Data
US 2014/0308343 A1 Oct. 16, 2014

Related U.S. Application Data

(62) Division of application No. 12/745,670, filed as application No. PCT/FR2008/001661 on Nov. 28, 2008.

(30) Foreign Application Priority Data

Nov. 30, 2007 (FR) ..................... 07 08399

(51) Int. Cl.
| | | |
|---|---|---|
| A61K 33/24 | (2006.01) | |
| A61K 47/26 | (2006.01) | |
| A61K 9/48 | (2006.01) | |
| A61K 9/51 | (2006.01) | |
| A61K 31/28 | (2006.01) | |
| A61K 31/282 | (2006.01) | |
| A61K 31/7052 | (2006.01) | |
| A61K 31/706 | (2006.01) | |
| A61K 31/7072 | (2006.01) | |
| A61K 31/708 | (2006.01) | |
| C07H 19/06 | (2006.01) | |
| C07H 19/10 | (2006.01) | |
| C07H 19/16 | (2006.01) | |

(52) U.S. Cl.
CPC ............ *A61K 47/26* (2013.01); *A61K 9/4816* (2013.01); *A61K 9/5123* (2013.01); *A61K 31/28* (2013.01); *A61K 31/282* (2013.01); *A61K 31/706* (2013.01); *A61K 31/708* (2013.01); *A61K 31/7052* (2013.01); *A61K 31/7072* (2013.01); *A61K 33/24* (2013.01); *C07H 19/06* (2013.01); *C07H 19/10* (2013.01); *C07H 19/16* (2013.01)

(58) Field of Classification Search
CPC .. A61K 31/28; A61K 31/282; A61K 31/7052; A61K 31/706
See application file for complete search history.

(56) References Cited

U.S. PATENT DOCUMENTS

| 5,019,394 A | * | 5/1991 | Hamaguchi et al. ......... 424/423 |
| 6,001,817 A |   | 12/1999 | Shaw |
| 6,534,486 B1 | * | 3/2003 | Allen et al. ..................... 514/46 |

FOREIGN PATENT DOCUMENTS

| WO | 01/32139 A | 5/2001 |
| WO | 2006/133092 | 12/2006 |
| WO | 2005/116043 A | 12/2008 |

OTHER PUBLICATIONS

Burger et al. (Nature Medicine, vol. 8, No. 1, Published Jan. 2002, pp. 81-84).*
Zhou (Antiviral Chemistry & Chemotherapy, pp. 375-383, published 2005).*
Avgoustakis, K., et al., "PLGA-mPEG Nanoparticles of Cisplatin: In vitro Nanoparticle degradation, in vitro drug release and in vivo drug residence in blood properties," Journal of Controlled Release, vol. 79, No. 1-3, Feb. 19, 2002, pp. 123-135.
Chabaud, Pauline, et al., "Cationic Nucleoside Lipids for Gene Delivery," Bioconjugate Chemistry, vol. 17, No. 2, Mar. 2006, pp. 467-472.
Barthelemy, Philippe, et al., "Supramolecular Assemblies with DNA," Pure and Applied Chemistry, vol. 77, No. 12, 2005, pp. 2133-2148.
Hird, G.S. et al., "Supramolecular Structures of Novel Carbohydrate-based Phospholipids," Journal of the American Chemical Society, vol. 122, No. 33, Aug. 23, 2000, pp. 8097-8098.
Steerenberg, P.A., et al., Liposomes as A Drug Carrier System for cis-Diamminedichloroplatinum (II). I. Binding Capacity, Stability and Tumor Cell Growth Inhibition in Vitro. International Journal of Pharmaceutics 40:51-62 (1987).
Campins et al. (New Journal of Chemistry, vol. 31, Published Aug. 16, 2007, pp. 1929-1934).
Burger et al. (Nature Medicine, vol. 8, No. 1, pp. 81-84, Published Jan. 2002).

* cited by examiner

*Primary Examiner* — Alma Pipic
(74) *Attorney, Agent, or Firm* — Browdy and Neimark, PLLC

(57) ABSTRACT

The invention relates to a method for preparing nanoparticles based on functional amphiphilic molecules or macromolecules, optionally in the presence of at least one colipide, enabling the encapsulation of therapeutic agents, especially anti-tumoral agents, and the use thereof for the transport and vectorization of therapeutic agents, especially anti-tumoral agents.

9 Claims, 3 Drawing Sheets

METHOD FOR PREPARING NANOPARTICLES BASED ON FUNCTIONAL AMPHIPHILIC MOLECULES OR MACROMOLECULES, AND THE USE THEREOF

This application is a divisional of Ser. No. 12/745,670 filed on Nov. 24, 2010, which is a 371 of PCT/FR08/001661 filed on Nov. 28, 2008, and claims foreign priority in French application 07/08399 filed on Nov. 30, 2007.

The invention relates to a process for the preparation of nanoparticles based on functional amphiphilic molecules or macromolecules and the use thereof for the transport or vectorization of therapeutic agents, in particular of anti-neoplastic agents.

Among the anti-neoplastic agents, cis-platin is an anti-neoplastic agent that is widely used, in particular for the treatment of solid tumours. However, its use is limited by its toxicity as well as the onset of an acquired resistance.

In order to overcome these drawbacks, different formulations have been proposed in the prior art: for example, the U.S. Pat. No. 5,178,876 describes platinum derivatives in the form of hydrophobic complexes intended for encapsulation in liposomes.

The U.S. Pat. No. 6,001,817 describes compositions containing cis-platin and a vector comprising at least one nucleoside or deoxynucleoside.

The U.S. Pat. No. 7,908,160 relates to cis-platin derivatives bound to ligands, the activity of which is reversible as a function of the bond to the ligand.

The application WO01/32139 describes compositions of cis-platin encapsulated in lipophilic nanoparticles obtained by repeated heating and freezing cycles, based on negatively charged natural lipids, in particular dioleyl-phosphatidylserine. It is indicated in this application that cis-platin forms, in water, positively charged aggregates having a higher solubility than the non-charged species, which allows their interaction with the negatively charged lipid membranes and the reorganization of the lipid membranes around the cis-platin aggregates.

However, there is still a need to solve the problems linked to the vectorization of therapeutic agents, in particular the anti-neoplastic agents.

In particular, a means is sought which allows transport of the therapeutic agents (in particular cis-platin and/or its derivatives) rapidly to the inside of the tumorous cells with a high pharmacological activity, whilst preserving the healthy cells, i.e. by reducing the neurological, renal, auditory, digestive, etc. toxicity, by simultaneously limiting the phenomena of the appearance of resistance to this therapeutic agent.

It is also sought to provide a vector having a sufficient stability over time to avoid the early release of the therapeutic agent and the drawbacks associated with the presence of the free therapeutic agent in the biological medium, in particular in terms of loss of activity and toxicity.

It has now been found that the use of nanoparticles formed from functional amphiphilic molecules or macromolecules allows the effective and rapid intracellular delivery of therapeutic agents and exhibited improved stability properties, in particular at 37° C., allowing a sustained vectorization of said therapeutic agents over time.

By "therapeutic agents", is meant, for example, a natural or synthetic molecule used for the prevention or treatment of a pathology or the restoration of a biological function, in vitro or in vivo, in particular in animals, including human beings, or also on isolated cells, with the exception of nucleic acids or fragments thereof.

Such a molecule can be chosen, for example, from the active ingredients of medicaments, in particular from anti-neoplastic agents such as, for example:

platinum complexes, among which there can in particular be mentioned cis-platin, carboplatin, oxaliplatin, nedaplatin, lobaplatin, etc. or ruthenium capable of binding to platinum complexes, or also inorganic complexes without platinum based on ruthenium II and/or III, titanium, for example titanocene dichloride, or gallium, for example the gallium salts such as gallium nitrate, gallium chloride, KP46, or iron derivatives, such as, for example, ferrocenium salts, nucleoside analogues containing iron, iron (II) complexes containing pyridyl-based pentadentate ligands, or cobalt derivatives, such as, for example, hexacarbonyl-dicobalt complexes, alkyne-cobalt complexes, Co(III) complex containing a nitrogen mustard ligand, or gold derivatives such as, for example, Auranofin, gold (I), (III) and (III) complexes, aurothioglucose, etc.

Advantageously, the use of nanoparticles formed from functional amphiphilic molecules or macromolecules of formula (I) for encapsulating these compounds and ensuring their intracellular delivery makes it possible to limit the phenomena of resistance to these compounds.

The platinum complexes, in particular cis-platin, are preferred therapeutic agents for the purposes of the invention.

Inorganic complexes based on ruthenium II and/or III, can be, for example, the complexes called NAMI-A, RAPTA-C, KP1019. Such non-platinum complexes are described in Ott I. and Gust R., Arch. Pharm. Chem. Life Sci. 2007, 340, 117-126; Reedijk J., Curr Opin Chem. Biol., 1999, 3, 236-40; Haimei Chen et al., J. Am. Chem. Soc., 2003, 125, 173-186.

Nucleoside analogues containing iron are described in Schlawe D. et al., Angew. Chem. Int. Ed., 2004, 1731-1734).

According to a first aspect the invention therefore relates to a process for encapsulating a therapeutic agent, preferably an anti-neoplastic agent, comprising the stages consisting of:

a) preparing a mixture of at least one functional amphiphilic compound of formula (I)

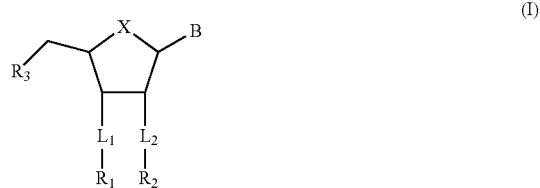

in which

X represents an oxygen or sulphur atom or a methylene group,

B represents a purine or pyrimidine base such as uracil, adenine, guanine, cytosine, thymine, hypoxanthine, or their derivatives, or also a non-natural mono- or bi-cyclic heterocyclic base each ring of which comprises 4 to 7 members, optionally substituted;

$L_1$ and $L_2$, identical or different, represent hydrogen, an oxycarbonyl —O—C(O)— group, a thiocarbamate —O—C(S)—NH— group, a carbonate —O—C(O)—O— group, a carbamate —O—C(O)—NH— group, an oxygen atom, a phosphate group, a phosphonate group or a heteroaryl group comprising 1 to 4 nitrogen atoms, unsubstituted or substituted by a linear or branched, saturated or unsaturated $C_2$-$C_{30}$ hydrocarbon chain, or also, $L_1$ and $L_2$, together, form a ketal group of formula

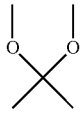

or also $L_1$ or $L_2$ represents hydrogen, and the other represents a hydroxy group or a heteroaryl group comprising 1 to 4 nitrogen atoms, unsubstituted or substituted by a linear or branched $C_2$-$C_{30}$ alkyl chain;

$R_1$ and $R_2$, identical or different, represent a linear or branched $C_2$-$C_{30}$ hydrocarbon chain, preferably $C_6$-$C_{25}$, in particular $C_8$-$C_{25}$, saturated or partially unsaturated, optionally completely or partially fluorinated, unsubstituted or substituted on the carbon at the end of the chain by a fluorine atom or by a benzyl or naphthyl ester or ether, or a diacyl chain in which each acyl chain is $C_2$-$C_{30}$, or a diacylglycerol, sphingosine or ceramide group, or when $L_1$ or $L_2$ represents hydrogen, and the other represents a hydroxy group or a heteroaryl group comprising 1 to 4 nitrogen atoms, $R_1$ and $R_2$ do not exist;

$R_3$ represents a hydroxy, amino, phosphate, phosphonate, phosphatidylcholine, O-alkyl phosphatidylcholine, thiophosphate, phosphonium, $NH_2$—$R_4$, $NHR_4R_5$ or $NR_4R_5R_6$ group in which $R_4$, $R_5$ and $R_6$, identical or different, represent a hydrogen atom or a linear or branched $C_1$-$C_5$ alkyl chain or linear or branched $C_1$-$C_5$ hydroxyalkyl, or a linear or branched $C_2$-$C_{30}$ alkyl chain optionally substituted by a hydroxy group, or a cyclodextrin radical, or a

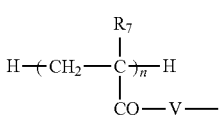

radical, in which V represents an —O—, —S—, or —NH— bond, $R_7$ represents H or $CH_3$, and n=1 to 500, or a —$(CH_2)_n$—V—$R_8$ group, in which $R_8$ represents a $C_2$-$C_{30}$ alkyl, and n=1 to 500, or a heteroaryl group containing 1 to 4 nitrogen atoms, unsubstituted or substituted by a $C_2$-$C_{30}$ alkyl, or by a $(CH_2)_m$—O—$(CH_2)_p$—$R_9$ group in which m=1 to 6 and p=0 to 10 and $R_9$ represents a cyclic ketal group containing 5 to 7 atoms, unsubstituted or substituted by at least one linear or branched $C_2$-$C_{30}$ alkyl or by a sterol radical, or also $R_3$ is bound by a covalent bond to another substituent $R_3$, identical or different, of another compound of formula (I), identical or different, in order to form a compound of formula (I) in the form of a dimer, and a therapeutic agent, preferably an anti-neoplastic agent,
b) subjecting said mixture to repeated heating and freezing cycles, so as to obtain nanoparticles containing said therapeutic agent, and
c) recovering the nanoparticles containing said therapeutic agent obtained in this way.

Figure 1:
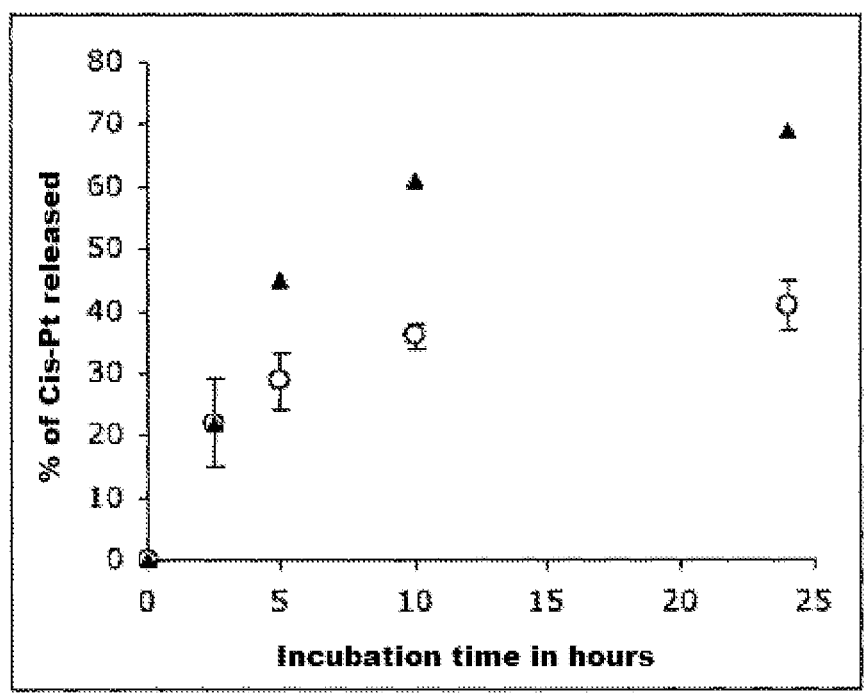
FIG. 1 is a graph of the release of cis-platin as a function of time.

Advantageously, it has been found that the molecular and/or macromolecular structures which constitute the compounds of formula (I), comprising at least one ligand of the therapeutic agent (nucleobase, nucleoside, modified nucleoside, nucleotides, oligonucleotide, heterocycle, etc) represented by the substituent B, and having an amphiphilic character due to the presence of at least one hydrophilic part (phosphate, carboxylate, etc), and of at least one hydrophobic part (hydrophobic segments which are single-stranded, double-stranded and polar parts derived from synthons of biological origin, etc.), making it possible to form stable nanoparticles with the therapeutic agent.

By combining the amphiphilic properties of the compounds of formula (I), the presence of ligands of the therapeutic agent (active ingredient) in these compounds and any electrostatic interactions between the therapeutic agents and these compounds, the nanoparticles obtained in this way have a structure which allows an effective and rapid intra-cell delivery of the encapsulated active ingredients, in particular anti-neoplastic agents.

Without wishing to restrict the invention to one theory, it can be postulated that the intermolecular interactions of the compounds of formula (I) lead to an increase in the cohesion forces on the surface of the nanoparticles, which results in a greater stability over time, under the conditions of use.

Advantageously, said nanoparticles also have a life span compatible with their use as a vector for a therapeutic agent.

In formula (I) above, n is advantageously comprised between 1 and 500, preferably comprised between 1 and 100, in particular comprised between 1 and 50, quite particularly comprised between 1 and 10.

By "linear or branched $C_1$-$C_5$ alkyl", is meant for example a methyl, ethyl, propyl, i-propyl, n-butyl, i-butyl, tert-butyl radical, preferably methyl or ethyl.

Also, in formula (I) above, the purine or pyrimidine base, or the non-natural heterocyclic base can be substituted by at least one substituent chosen, for example, from a halogen, an amino group, a carboxy group, a carbonyl group, a carbonylamino group, a hydroxy, azido, cyano, alkyl, cycloalkyl, perfluoroalkyl, alkyloxy (for example, methoxy), oxycarbonyl, vinyl, ethynyl, propynyl, acyl group etc.

By "non-natural heterocyclic base" is meant a base other than uracil, adenine, guanine, cytosine, thymine or hypoxanthine, which does not exist in nature.

By "heteroaryl group containing 1 to 4 nitrogen atoms", is meant a monocyclic or bicyclic, aromatic or partially unsaturated, carbocyclic group containing 5 to 12 atoms, interrupted by 1 to 4 nitrogen atoms, in particular the pyrazole, triazole, tetrazole or imidazole groups.

For the preparation of the compounds of formula (I), reference can be made to the application WO 2005/116043, which describes different access routes to this type of compounds (see in particular pp. 8-17 and examples).

The process according to the invention can comprise the stages implemented under the following general conditions:

the compound of formula (I), is put in solution in an organic solvent in order to form a lipid mixture, then, after removal, evaporation is carried out in order to form a film;

in parallel, the desired quantity of therapeutic agent, preferably an anti-neoplastic agent, is put in solution in distilled water;

the lipid film is rehydrated in the solution of therapeutic agent, preferably an anti-neoplastic agent. A clear solution is obtained by sonication and heating;

the solution is cooled down rapidly, for example by immersion in liquid nitrogen. This heating/cooling cycle is preferably carried out 1 to 10 times, in particular 5 to 10 times, in particular 10 times.

The solution obtained is centrifuged. The supernatant is separated. After several centrifugations, the pellet is dried.

The organic solvent can be chosen, for example, from the usual organic solvents in the field, such as, for example, chloroform, an alcohol such as methanol or ethanol, etc.

The heating is carried out, preferably, to a temperature of the order of 20° C. to 80° C., and the cooling to a temperature of the order of −190° C. (liquid nitrogen) to 0° C. (ice). An appropriate heating/cooling cycle can, for example, be 45° C. for the heating and −78° C. for the cooling.

Preferably, the therapeutic agent is chosen from the platinum complexes (cis-platin, carboplatinum, etc.), cis-platin being particularly preferred, or ruthenium capable of binding to platinum complexes, or also the abovementioned inorganic complexes without platinum based on ruthenium II or III, titanium, gallium, cobalt, iron or gold.

The molar ratio R of the compound of formula (I)/therapeutic agent can be comprised, for example, between 0.01 and 50, in particular R=0.2.

The nanoparticles obtained can be optionally extruded on polycarbonate filter having, for example, a pore diameter of the order of 100 or 200 nm.

In this way solid nanoparticles are obtained which are constituted by a core rich in therapeutic agent (active ingredient) surrounded by one or more lipid layers constituted by the functional amphiphilic compound of formula (I) as defined above, with or without co-lipid.

Said solid nanoparticles, constituted by a core rich in therapeutic agent, preferably an anti-neoplastic agent, in particular a platinum complex, surrounded by one or more lipid layers constituted by the functional amphiphilic compound of formula (I) as defined above, with or without co-lipid, represent a subsequent subject of the invention.

In the case of a multi-layer surround, all the lipid layers are constituted by the same lipids (compound of formula (I) with or without co-lipid).

According to an aspect of the invention, at least one co-lipid will be used in the lipid mixture, in addition to the compound of formula (I).

By "co-lipid", is meant a compound used in combination with the compound of formula (I), which contributes to the production of the structure of the lipid layers(s) of the nanoparticle.

Preferably, a zwitterionic co-lipid will be used.

Said co-lipid can be, for example, chosen from dioleylphosphatidylcholine (DOPC) or dioleylphosphatiduridine phosphatidylcholine (DOUPC), in combination with the compound of formula (I) in order to form the lipid layer(s) of the nanoparticle.

These compounds can play the role of co-lipid when they are used in mixture with a compound of formula (I). Alternatively, they can be included in formula (I), such as, for example, dioleylphosphatiduridinephosphatidylcholine (DOUPC). In this case, they will either play the role of compound of formula (I) or, in combination with another compound of formula (I), the role of co-lipid.

According to a preferred aspect of the process, said lipid mixture contains solely at least one compound of formula (I) and does not contain co-lipid.

Preferably, the therapeutic agent will be used at a concentration of the order of 0.1 ng/mL to 10 mg/mL in the aqueous phase, so that the intracellular delivery of the active ingredient is significant.

The preferred compounds of formula (I) are those in which X represents oxygen.

The compounds of formula (I) in which B represents thymine or adenine are also preferred compounds.

Among the compounds of formula (I) which are particularly advantageous for the purposes of the invention, the compounds of formula (I) can be mentioned in which:

X and B are as defined above;

$L_1$ represents a phosphate group, $L_2$ represents hydrogen, $R_1$ represents a $C_2$-$C_{30}$ alkyl group or a diacyl group in which each acyl chain is $C_2$-$C_{30}$, and $R_3$ is a hydroxy group; or $L_1$ and $L_2$ represent an oxygen atom, $R_1$ and $R_2$ represent hydrogen and $R_3$ represents a triazole, tetrazole, pyrazole or imidazole group substituted by a $C_2$-$C_{30}$ alkyl group, or $L_1$ represents a triazole, tetrazole, pyrazole or imidazole group, $L_2$ represents hydrogen, $R_1$ represents a $C_2$-$C_{30}$ alkyl group and $R_3$ is a hydroxy group, or $L_1$ represents a hydroxy group, $L_2$ represents hydrogen and $R_3$ is a triazole group substituted by a $C_2$-$C_{30}$ alkyl chain, optionally substituted by a hydroxy group, or $R_3$ is a group or a —$(CH_2)_n$—V—$R_8$ group, in which V represents —O— or —NH— and $R_8$ represents a $C_2$-$C_{30}$ alkyl, or $L_1$ represents a hydroxy group, $L_2$ represents hydrogen and $R_3$ is a triazole group substituted by a $(CH_2)_m$—O—$(CH_2)_p$—$R_9$ group in which m=1 to 6 and p=0 to 10 and $R_9$ represents a cyclic ketal group containing 5 to 7 atoms, unsubstituted or substituted by at least one linear or branched $C_2$-$C_{30}$ alkyl group or by a sterol radical, or $L_1$ represents a hydroxy group, $L_2$ represents hydrogen and $R_3$ is a triazole group substituted by a $(CH_2)_m$—O—$(CH_2)_p$—$R_9$ group in which m=1 to 6 and p=0 to 10 bound by covalent bond to another identical substituent $R_3$ of another identical compound of formula (I), in order to form a compound of formula (I) in the form of a dimer, or $L_1$ represents a phosphate group, $L_2$ represents hydrogen $R_1$ represents a diacyl chain in which each diacyl chain is $C_2$-$C_{30}$, and $R_3$ is a hydroxy group, which are new compounds.

The compounds of formula (I) in which the substituent $L_1$ or the substituent $R_3$ is constituted by or comprises a triazole group, unsubstituted or substituted, are also preferred new compounds for the purposes of the process according to the invention.

The above compounds are new compounds which represent a subject of the invention, as well as the nanoparticles comprising these compounds and a therapeutic agent, in particular an anti-neoplastic agent, in particular the platinum complexes (such as, for example cis-platin, carboplatin, oxaliplatin, nedaplatin, lobaplatin), or ruthenium capable of binding to the platinum complexes, or also the abovementioned inorganic complexes without platinum based on ruthenium, titanium, gallium, cobalt, iron or gold. Cis-platin is a preferred anti-neoplastic agent for the purposes of the invention.

The compounds of formula (I) can comprise purine or pyrimidine base derivatives having an anti-neoplastic activity, such as, for example, aracytosine (AraC), 5-fluorouracil (5-FU), Iododeoxyuridine (IdU), 2'-deoxy-2'-methylidenecytidine (DMDC) or 5-chloro-6-azido-5,6-dihydro-2'-deoxyuridine.

A subject of the invention is also the use of the nanoparticles capable of being obtained by the process described above, for the transport or vectorization of therapeutic agents, in particular anti-neoplastic agents.

In particular, the invention relates to the use of the nanoparticles capable of being obtained by the process described above, for the intracellular delivery of therapeutic agents, in particular anti-neoplastic agents.

The invention also relates to the use of the nanoparticles capable of being obtained by the above process, for the preparation of anti-neoplastic medicaments.

The invention also relates to the nanoparticles capable of being obtained by the above process, for the treatment of tumour diseases, in particular cancers, such as, for example, cancers of the ovary, testicle, colon, cervix, lung, or adenosarcoma etc.

The invention is illustrated non-limitatively by the examples below.

All of the starting products originate from suppliers of chemical products (Aldrich, Alfa Aesar and Avanti Polar Lipid) and are used without subsequent purification. The solvents were used without additional distillation. The synthesized compounds were characterized using standard spectroscopic analytical methods such as NMR $^1$H at 300.13 MHz, $^{13}$C at 75.46 MHz and $^{31}$P at 121.49 MHz) and mass spectroscopy (Characteristics). The chemical shifts (δ) in NMR are expressed in ppm and relative to TMS. The coupling constants J in NMR $^1$H are expressed in Hz. Merck RP-18 F254s plates were used for the thin layer chromatography (TLC). SEPHADEX LH-20 (25-100 μm) silica was used for the purifications by quantitative chromatographies.

The examples below, entitled "Preparation" describe the preparation of synthesis intermediates used for preparing the compounds of formula (I). The preparation of the compounds of formula (I) is then described in the synthesis examples entitled "Example".

Preparation 1

5'-paratoluenesulphonylthymidine

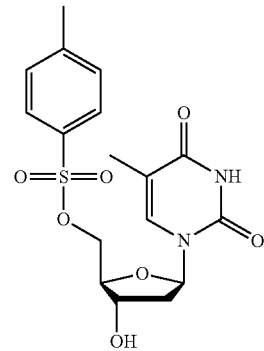

2 g of thymidine (8.26 mmol) in 0.1 M solution is introduced into anhydrous pyridine in a two-necked flask under an anhydrous nitrogen atmosphere. The solution is then cooled down to 0° C. and 3.935 g of paratoluene sulphonic acid chloride (2.5 equivalents, 20.6 mmol) are added in small portions. The reaction medium is left to return to ambient temperature, then stirred for 10 hours. The reaction is then stopped by the addition of 10 mL of methanol, stirring is maintained for 30 min. 50 mL of $CH_2Cl_2$ is added to the mixture then it is washed successively with 20 mL of a 5% solution of $NaHCO_3$, 20 mL of a saturated solution of NaCl and 20 mL of a 5% solution of $NaHCO_3$. The solvent is eliminated under reduced pressure. The expected compound is obtained pure by recrystallization from methanol.

Rf: 0.47 (AcOEt/MeOH 9/1)

The yield is 75%.

NMR $^1$H (300.13 MHz, DMSO $d_6$): δ 1.77 (s, 3H, $CH_3$), δ 2.11 (m, 2H, $CH_2$), δ 2.42 (s, 3H, $CH_3$), δ 3.52 (t, j=6 Hz, 4H, $CH_2$), δ 4.18 (m, 1H, CH), δ 4.25 (m, 3H, CH, $CH_2$), δ 5.42 (s, 1H, OH), δ 6.15 (t, j=6 Hz, H, CH), δ 7.38 (s, 1H, CH), δ 7.46 (s, 1H, CH), δ 7.49 (s, 1H, CH), δ 7.78 (s, 1H, CH), δ 7.81 (s, 1H, CH), δ 11.28 (s, 1H, NH).

NMR $^{13}$C (75.47 MHz, DMSO $d_6$): δ 12.5 ($CH_3$), δ 21.6 ($CH_3$), δ 38.9 ($CH_2$), δ 70.4 ($CH_2$), δ 70.6 (CH), δ 83.7 (CH), δ 84.5 (CH), δ 110.3 (C), δ 128.1 (CH ar), δ 130.6 (2 CH ar), δ 132.6 (C ar), δ 136.4 (C ar), δ 145.6 (C), δ 150.8 (C=O), δ 164.1 (C=O).

High resolution MS [M+H]$^+$: 397.1

Preparation 2

2'-deoxy-5'-toluenesulphonyladenosine

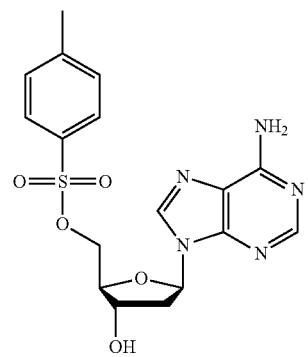

2 g of 2'-deoxyadenosine (8 mmol) in a 0.1 M solution is introduced into anhydrous pyridine in a two-necked flask under an anhydrous nitrogen atmosphere. The solution is then cooled down to 0° C. and 3.793 g of paratoluene sulphonic acid chloride (2.5 equivalents, 20 mmol) are added by small portions. The reaction medium is left to return to ambient temperature, then stirred for 10 hours. The reaction is then stopped by the addition of 10 mL of methanol, stirring is maintained for 30 min. 50 mL of $CH_2Cl_2$ is added to the mixture then it is washed successively with 20 mL of a 5% solution of $NaHCO_3$, 20 mL of a saturated solution of NaCl and 20 mL of a 5% solution of $NaHCO_3$. The solvent is eliminated under reduced pressure. The expected compound is obtained pure by recrystallization from methanol. 2.1 g of a white product is isolated in this way.

Rf: 0.37 (AcOEt/MeOH 9/1)

The yield is 63%.

Preparation 3

5' azido-5'-deoxythymidine

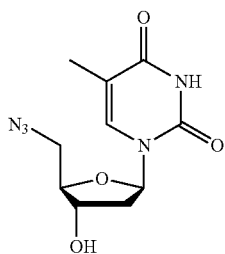

2 g of 5'-paratoluenesulphonylthymidine (5 mmol) as described in Preparation 1 in a 0.1 M solution is introduced into DMF in a two-necked flask provided with a condenser and under an anhydrous nitrogen atmosphere. 1.3 g of sodium azide (4 equivalents, 20 mmol) is added. The solution is then stirred and heated at 110° C. for 10 hours. The mixture is cooled down to ambient temperature. 50 mL of $CH_2Cl_2$ is added to the mixture then it is washed successively with twice 15 mL of water then with 15 mL of a saturated aqueous solution of NaCl. The organic phase is dried over sodium sulphate then the solvent is eliminated under reduced pressure. The expected compound is obtained pure by recrystallization from methanol. 0.8 g of a white solid is obtained in this way.

Rf: 0.47 (AcOEt/MeOH 9/1)

The yield is 60%.

MS $[M+H]^+$: 268.1

Preparation 4

5'-azido-5',2'-dideoxyadenosine

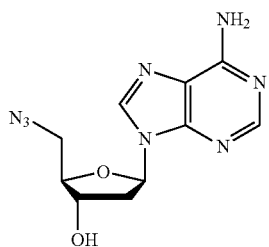

2 g of 2'-deoxy-5'-paratoluenesulphonyladenosine as described in Preparation 2 (5 mmol) in a 0.1 M solution is introduced into DMF in a two-necked flask provided of a condenser and under an anhydrous nitrogen atmosphere. 1.3 g of sodium azide (4 equivalents, 20 mmol) is added. The solution is then stirred and heated at 110° C. for 10 hours. The mixture is cooled down to ambient temperature. 50 mL of $CH_2Cl_2$ is added to the mixture then it is washed successively with twice 15 mL of water then with 15 mL of a saturated aqueous solution of NaCl. The organic phase is dried over sodium sulphate then the solvent is eliminated under reduced pressure. The expected compound is obtained pure by recrystallization from methanol. 0.8 g of a white solid is obtained in this way.

Rf: 0.37 (AcOEt/MeOH 9/1)

The yield is 60%.

High resolution MS $[M+H]^+$: calculated mass: 277.1161, measured mass: 277.1157

Preparation 5

1-propargyloxyoctadecane

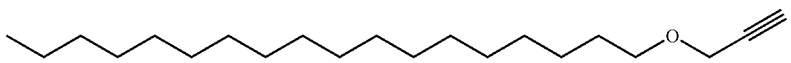 [SMILES: C#CCOCCCCCCCCCCCCCCCCCC]

673 mg of propargylic alcohol (12 mmol) in a 0.5 M solution is introduced into DMF in a clean and dry flask under an anhydrous nitrogen atmosphere. The solution is then cooled down to 0° C. and 180 mg of sodium hydride (0.625 equivalent, 7.5 mmol) are added by small portions. The reaction medium is left to return to ambient temperature. 2 g of 1-bromo-octadecane (0.5 equivalent, 6 mmol) are added. Stirring is maintained for 5 hours. The reaction is then stopped by the addition of 10 mL of methanol and stirring is maintained for 30 min. 50 mL of $CH_2Cl_2$ is added to the mixture then it is washed successively with twice 20 mL and 20 mL of a saturated solution of NaCl. The organic phase is then dried over $Na_2SO_4$ then the solvent is eliminated under reduced pressure. The expected compound is obtained pure after separation on a chromatographic column (hexane). 1.2 g of a white product is isolated in this way.

Rf: 0.82 (Hexane)

The yield is 65%.

NMR $^1$H (300.13 MHz, CDCl$_3$): δ 0.90 (t, j=6 Hz, 3H, CH$_3$), δ 1.28 (s, 30H, CH$_2$), δ 1.61 (m, 2H, CH$_2$), δ 2.43 (t, j=3 Hz, 1H, CH), δ 3.53 (t, j=6 Hz, 2H, CH$_2$), δ 4.15 (d, j=3 Hz, 2H, CH$_2$).

NMR $^{13}$C (75.47 MHz, CDCl$_3$): NMR $^{13}$C (75.47 MHz, CDCl$_3$): δ 14.2 (CH$_2$), δ 22.7 (CH$_2$), δ 26.1 (CH$_2$), δ 29.4 (CH$_2$), δ 29.5 (CH$_2$), δ 29.6 (CH$_2$), δ 32.0 (CH$_2$), δ 58.0 (CH$_2$), δ 70.4 (CH$_2$), δ 74.1 (CH), δ 80.1 (O).

Preparation 6

1,12-propargyloxydodecane 12-propargyloxydodecan-1-ol 1 g of dodecan-1,12-diol (5 mmol) in a 0.5 M solution is introduced into DMF in a clean and dry flask, under an anhydrous nitrogen atmosphere. The solution is then cooled down to 0° C. and 360 mg of hydrogen hydride (3 equivalents, 15 mmol) is added by small portions. The reaction medium is left to return to ambient temperature. 1.49 g of propargyl bromide (2.5 equivalents, 12.5 mmol) is added. Stirring is maintained for 5 hours. The reaction is then stopped by the addition of 10 mL of methanol, stirring is maintained for 30 min. 50 mL of CH$_2$Cl$_2$ is added to the mixture then it is washed successively with twice 20 mL and 20 mL of a saturated solution of NaCl. The organic phase is then dried over Na$_2$SO$_4$ then the solvent is eliminated under reduced pressure. The products obtained are then separated on a chromatographic column (Hex/ActEth 9/1). Two products are isolated, namely 370 mg of a brown oil corresponding to 1,12-Propargyloxydodecane and 430 mg of a brown solid corresponding to 12-propargyloxydodecan-1-ol.

1,12-propargyloxydodecane

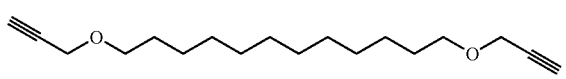 [SMILES: C#CCOCCCCCCCCCCCCOCC#C]

Rf: 0.53 (Hexane/AcOtEt 9/1)

The yield is 27%.

NMR $^1$H (300.13 MHz, CDCl$_3$): δ 1.31 (m, 16H, CH$_2$), δ 1.61 (m, 4H, CH$_2$), δ 2.43 (t, j=3 Hz, 1H, CH), δ 3.52 (t, j=6 Hz, 4H, CH$_2$), δ 4.15 (d, j=3 Hz, 4H, CH$_2$).

NMR $^{13}$C (75.47 MHz, CDCl$_3$): δ 26.1 (CH$_2$), δ 29.4 (CH$_2$), δ 29.5 (CH$_2$), δ 29.6 (CH$_2$), δ 58.0 (CH$_2$), δ 70.3 (CH$_2$), δ 74.1 (CH), δ 80.1 (C).

12-propargyloxydodecan-1-ol

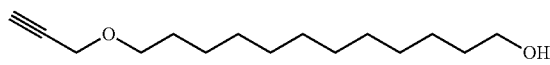 [SMILES: C#CCOCCCCCCCCCCCCO]

Rf: 0.10 (Hexane/AcOtEt 9/1)

The yield is 36%.

NMR $^1$H (300.13 MHz, CDCl$_3$): δ 1.32 (m, 16H, CH$_2$), δ 1.59 (m, 4H, CH$_2$), δ 2.43 (t, j=3 Hz, 2H, CH), δ 3.52 (t, j=6 Hz, 2H, CH$_2$), δ 3.65 (t, j=6 Hz, 2H, CH$_2$), δ 4.15 (d, j=3 Hz, 2H, CH$_2$).

NMR $^{13}$C (75.47 MHz, CDCl$_3$): δ 25.8 (CH$_2$), δ 26.0 (CH$_2$), δ 29.4 (2 CH$_2$), δ 29.5 (2 CH$_2$), δ 29.6 (CH$_2$), δ 32.7 (CH$_2$), δ 57.9 (CH$_2$), δ 62.7 (CH$_2$), δ 70.2 (CH$_2$), δ 74.2 (CH), δ 79.9 (C).

Preparation 7 o-propargylcholesterol

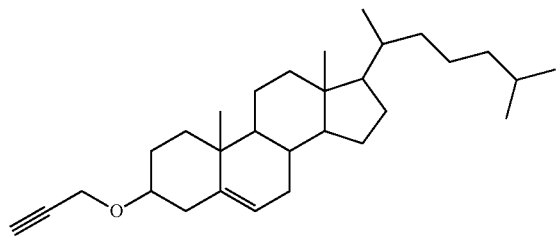 [SMILES: C#CCOC1CCC2(C)C(=CCC3C2CCC2(C)C(C(C)CCCC(C)C)CCC32)C1]

500 mg of cholesterol (1.3 mmol) in a 0.5 M solution is introduced into DMF in a clean and dry flask, under an anhydrous nitrogen atmosphere. The solution is then cooled down to 0° C. and 47 mg of sodium hydride (1.5 equivalents, 2 mmol) is added by small portions. The reaction medium is left to return to ambient temperature. 238 mg of propargyl bromide (1.5 equivalents, 2 mmol) is added. Stirring is maintained for 5 hours. The reaction is then stopped by the addition of 10 mL of methanol and stirring is maintained for 30 min. 50 mL of CH$_2$Cl$_2$ is added to the mixture then it is washed successively with twice 20 mL of a saturated solution of NaCl. The organic phase is then dried over Na$_2$SO$_4$ then the solvent is eliminated under reduced pressure. The expected compound is obtained after purification on a chromatographic column (Hexane/AcOEt 8/2). 215 mg of a white product are isolated in this way.

Rf: 0.83 (Hexane/AcOEt 8/2)

The yield is 39%.

EXAMPLE 1

Thymidine 3'-(1,2-dimyristoyl-sn-glycero-3-phosphate) (di c14dT)

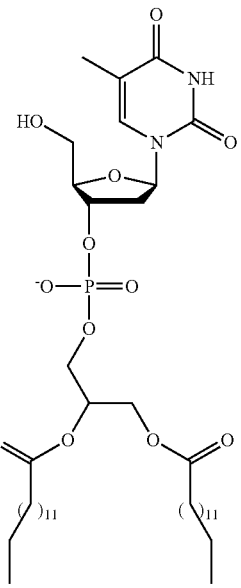

5'-O-(4,4'-dimethoxytrityl)-2'-deoxythymidine, 3'-[(2-cyano-ethyl)-N,N-diisopropyl)] phosphoramidite (0.500 g, 1 eq, 0.67 mmol), 1,2-dimyristoyl-sn-glycerol (0.447 g, 1.3 eq, 0.87 mmol) and a 0.45 M solution of tetrazole in acetonitrile (2 mL, 1.3 eq, 0.87 mmol) are dissolved in 4 mL of anhydrous acetonitrile under nitrogen. The reaction medium is magnetically stirred for 24 hours at ambient temperature. The mixture is then oxidized by the addition of 43 mL of a 0.02M solution of diiodine in THF/Pyr/H$_2$O. After 12 hours at ambient temperature, the solvent is evaporated off under vacuum. The residue is dissolved in 8 mL of dichloromethane. Then, 0.2 mL of 1,5-diazabicyclo[5.4.0]undec-7-ene (DBU) (1.3 eq, 0.87 mmol) is added to the reaction medium over 5 hours. The reaction medium is washed with a 0.1N solution of HCl then with a saturated solution of Na$_2$S$_2$O$_7$. The organic phase is concentrated under vacuum. The compound is obtained after purification by flash chromatography (381 mg) using an elution gradient (MeOH/DCM 9:1 to 1:1).

The yield is 69%.

Rf: 0.34 (DCM/MeOH 9:1)

NMR 1H (300 MHz CDCl3): δ in ppm 0.84 (t, 6H, J=6.92 Hz, 2*CH$_3$), 1.21 (m, 40H, 20*CH$_2$), 1.42 (dd, 4H, J1=8.45 Hz, J2=15.68 Hz, 2*CH2), 1.89 (s, 3H, Me), 2.30 (dd, 4H, J1=7.43 Hz, J2=15.92 Hz, 2*CH2), 2.83 (t, 2H, J=5.84, H2'), 3.84 (m, 1H, H3'), 4.09-4.35 (m, 7H, 2*CH$_2$ (glycerol), H4', H5'), 5.27 (s, 1H, CHglycerol), 6.22 (t, 1H, J=6.81 Hz, H1'), 7.61 (s, 1H, Hbase).

NMR 13C (75 MHz, CDCl3): δ in ppm 19.29 (CH$_3$), 23.71 (CH$_2$), 26.57 (CH$_2$), 28.73 (CH$_2$), 32.76 (CH$_2$), 37.85 (CH$_2$), 48.90 (CH$_2$), 166.15 (C=O).

NMR 31P (121 MHz, CDCl3): δ in ppm 0.61.

High Resolution Mass FAB–theoretical m/z=815.4823 observed m/z=815.4794.

EXAMPLE 2

Thymidine 3'-(1,2-dipalmitoyl-sn-glycero-3-phosphate) (di c16dT)

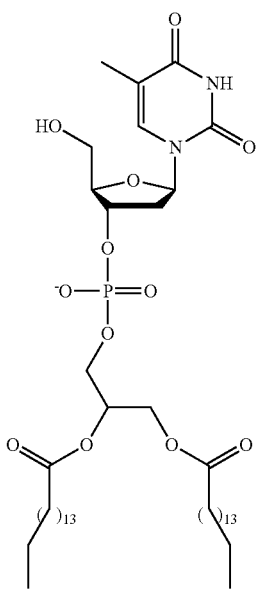

5'-O-(4,4'-dimethoxytrityl)-2'-deoxythymidine,3'-[(2-cyano-ethyl)-N,N-diisopropyl)] phosphoramidite (0.500 g, 1 eq, 0.67 mmol), 1,2-dipalmitoyl-sn-glycerol (0.496 g, 1.3 eq, 0.87 mmol/solubilized in 3 mL of THF) and a 0.45 M solution of tetrazole in acetonitrile (2 mL, 1.3 eq, 0.87 mmol) are dissolved in 3 mL of anhydrous acetonitrile under nitrogen. The reaction medium is magnetically stirred for 24 hours at ambient temperature and under nitrogen. The mixture is then oxidized by the addition of 43 mL of a 0.02M solution of diiodine in THF/Pyr/H$_2$O. After 12 hours at ambient temperature, the solvent is evaporated off under vacuum and dried under P$_2$O$_5$ overnight using a pump. The residue is dissolved in 8 mL of dichloromethane. Then, 0.2 mL of 1,5-diazabicyclo[5.4.0]undec-7-ene (DBU) (1.3 eq, 0.87 mmol) is added to the reaction medium over 5 hours. The reaction medium is washed with a 0.1N solution of HCl then with a saturated solution of Na$_2$S$_2$O$_3$. The organic phase is concentrated under vacuum. The compound is obtained after purification by flash chromatography (180 mg) using an elution gradient (MeOH/DCM 98:2 to 1:1).

The yield is 24%.

Rf: 0.3 (DCM/MeOH 8:2)

NMR 1H (300 MHz, CDCl3): δ in ppm 0.88 (t, 6H, J=6.9 Hz, 2*CH$_3$), 1.25 (m, 48H, 24*CH$_2$), 1.42 (dd, 4H, J1=8.4 Hz, J2=15.6 Hz, 2*CH2), 1.90 (s, 3H, Me), 2.33 (m, 4H, 2*CH$_2$), 2.83 (t, 2H, J=5.6 Hz, H$_2$'), 3.84 (m, 1H, H3'), 4.09-4.35 (m, 7H, 2*CH$_2$ (glycerol), H$_4$', H$_5$'), 5.27 (s, 1H, CH glycerol), 6.21 (t, 1H, J=6.7 Hz, H1'), 7.54 (s, 1H, H base).

NMR 1H(CDCl3): δ in ppm 12.4 (CH$_3$ base), 14.1 (CH$_3$ chain), 19.6 (CH$_2$), 19.7 (CH$_2$), 22.6 (CH$_2$), 24.8 (CH$_2$), 29.1-29.6 (CH$_2$), 31.9 (CH$_2$), 33.9 (CH$_2$), 34.1 (CH$_2$), 61.5 (CH$_2$), 61.7 (CH$_2$), 62.5 (CH$_2$), 62.6 (CH$_2$), 66.1 (CH$_2$), 66.2 (CH$_2$), 69.1 (CH), 78.8 (CH), 85.5 (CH), 86.1 (CH), 111.3 (C base), 136.8 (CH base), 150.5 (C=O base), 164.1 (C=O base), 173.0 (C=O chain), 173.5 (C=O chain).

NMR 31P (121 MHz, CDCl3): δ in ppm 2.1.

Mass ESI–: theoretical m/z=872.5 observed m/z=871.3.

EXAMPLE 3

5'-(4-Hexadecyloxymethyl-[1,2,3]triazol-1-yl)-5',2' dideoxythymidine

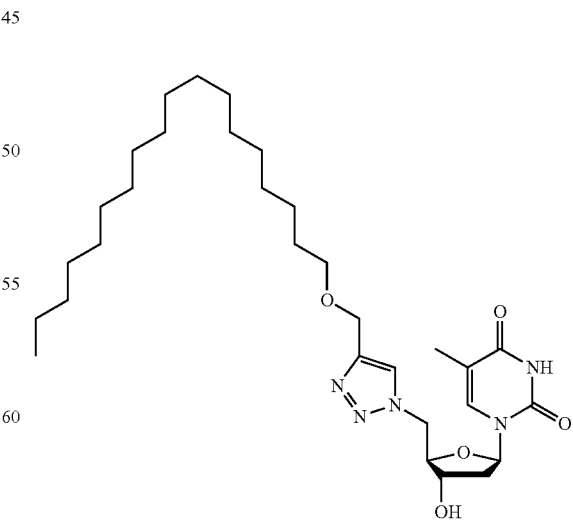

200 mg of 5'-azido-5-deoxythymidine as described in Preparation 3 (0.75 mmol) and 231 mg of 1-propargyloxyoctadecane as described in the Preparation 5 (1 equivalent) in a 0.1 M solution are introduced into a mixture of THF and water (1/1) in a flask. Then, the following are added successively: 30 mg of sodium ascorbate (0.2 equivalents, 0.15 mmol) and 12 mg of copper sulphate (0.1 equivalent, 0.075 mmol). The reaction medium is stirred and heated at 60° C. for 5 hours. The mixture is then cooled down to ambient temperature. The reaction medium is immediately adsorbed on silica and the solvent eliminated by evaporation. 180 mg of a white solid are obtained after chromatography on a silica column (AcOEt/MeOH 8/2).

Rf: 0.72 (AcOEt/MeOH 8/2)

The yield is 42%.

High resolution MS [M+H]$^+$: calculated mass: 576.4125, measured mass: 576.4120

EXAMPLE 4

5'-(4-Hexadecyloxymethyl-[1,2,3]triazol-1-yl)-5',2'-dideoxyadenosine

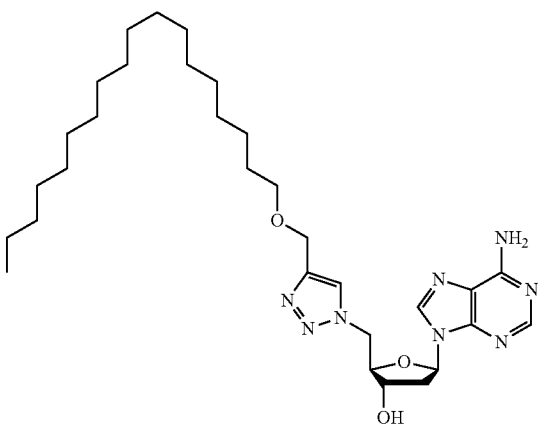

200 mg of 5'-azido-5',2'-dideoxyadenosine as described in Preparation 4 (0.72 mmol) and 223 mg of 1-propargyloxyoctadecane as described in Preparation 5 (1 equivalent) in a 0.1 M solution are introduced in a mixture of THF and water (1/1) in a flask. Then, the following are added successively: 30 mg of sodium ascorbate (0.2 equivalents, 0.15 mmol) and 12 mg of copper sulphate (0.1 equivalent, 0.075 mmol). The reaction medium is stirred and heated at 60° C. for 5 hours, then the mixture is cooled down to ambient temperature. The reaction medium is immediately adsorbed on silica and the solvent eliminated by evaporation. 150 mg of a white solid are obtained after column chromatography (AcOEt/MeOH 8/2).

Rf: 0.65 (AcOEt/MeOH 8/2)

The yield is 35%.

NMR $^1$H (300.13 MHz, CDCl$_3$): δ 0.89 (t, j=6 Hz, 3H, CH$_3$), δ 1.26 (m, 30H, CH$_2$), δ 1.55 (m, 2H, CH$_2$), δ 2.54 (m, 1H, CH$_2$), δ 3.06 (m, 1H, CH$_2$), δ 3.45 (t, j=6 Hz, 2H, CH$_2$), δ 4.50 (m, 4H, CH$_2$, CH), δ 4.89 (m, ???), δ 5.88 (s, 2H, NH$_2$), δ 6.40 (t, j=6 Hz, 1H, CH), δ 7.42 (s, 1H, CH), δ 7.81 (s, 1H, CH), δ 8.35 (s, 1H, CH).

High resolution MS [M+H]$^+$: calculated mass: 585.4241, measured mass: 585.4254

EXAMPLE 5

5'-(4-(1-hydroxy-hexyl)-[1,2,3]triazol-1-yl)-5',2' dideoxythymidine

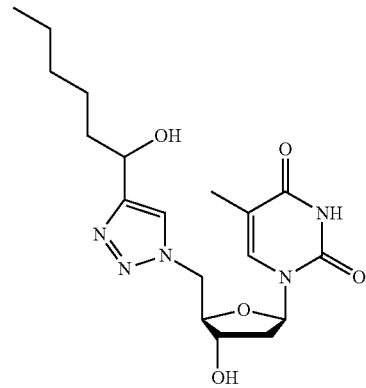

215 mg of 5'-azido-5'-deoxythymidine as described in Preparation 3 (0.8 mmol) and 101 mg of the racemic mixture of oct-1-yn-3-ol (1 equivalent) in a 0.1 M solution in a THF/water mixture (1/1) are introduced into a flask. Then, the following are added successively: 31.5 mg of sodium ascorbate (0.2 equivalent, 0.15 mmol) and 13 mg of copper sulphate (0.1 equivalent, 0.075 mmol). The reaction medium is stirred and heated at 60° C. for 5 hours. The mixture is then cooled down to ambient temperature. The reaction medium is then immediately adsorbed on silica and the solvent eliminated by evaporation. The compound is obtained pure by column chromatography (AcEt/MeOH 85/15). 255 mg of a white solid is obtained.

Rf: 0.48 (AcOEt/MeOH 85/15)

The yield is 78%.

NMR $^1$H (300.13 MHz, DMSO d$_6$): δ 0.83 (t, j=6 Hz, 3H, CH$_3$), δ 1.24 (m, 6H, CH$_2$), δ 1.68 (m, 2H, CH$_2$), δ 1.81 (s, 3H, CH$_3$), δ 4.06 (m, 1H, CH), δ 4.27 (m, 1H, CH), δ 4.62 (m, 3H, CH$_2$, CH), δ 5.2 (d, j=6 Hz, 1H, OH), δ 5.5 (s, 1H, OH), δ 6.17 (t, j=6 Hz, 1H, CH), δ 7.37 (s, 1H, CH), δ 7.89 (s, 1H, CH).

NMR $^{13}$C (75.47 MHz, DMSO d$_6$): δ 12.5 (CH$_3$), δ 14.4 (CH$_3$), δ 22.6 (CH$_2$), δ 25.1, δ 31.7 (CH$_2$), δ 38.4 (CH$_2$), δ 51.6 (CH$_2$—N), δ 66.0 (CH—O), δ 71.3 (C), δ 84.4, δ 84.5, δ 110.3 (=C—N), δ 122.8, δ 136.4, δ 150.9, δ 152.4, δ 164.1.

High resolution MS [M+Na]$^+$: calculated mass: 416.1910, measured mass: 416.1897

EXAMPLE 6

5'-(4-(hexyl)-[1,2,3]triazol-1-yl)-5',2' dideoxythymidine

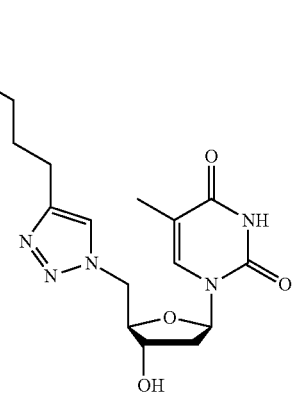

200 mg of 5'-azido-5'-deoxythymidine as described in Preparation 3 (0.75 mmol) and 82.65 mg of non-1-yne (1 equivalent) in a 0.1 M solution are introduced into a THF water mixture (1/1) in a flask. The following are added successively: 30 mg of sodium ascorbate (0.2 equivalent, 0.15 mmol) and 12 mg of copper sulphate (0.1 equivalent, 0.075 mmol). The reaction medium is stirred and heated at 60° C. for 5 hours. The mixture is then cooled down to ambient temperature. The reaction medium is immediately adsorbed on silica and the solvent eliminated by evaporation. The compound is obtained pure by column chromatography (AcOEt/MeOH 8/2). 130 mg of a white solid is obtained.

Rf: 0.62 (AcOEt/MeOH 8/2)

The yield is 46%.

High resolution MS [M+H]$^+$: calculated mass: 576.4125, measured mass: 576.4120

EXAMPLE 7

5'-(4-(heptyl)-[1,2,3]triazol-1-yl)-5',2' dideoxythymidine

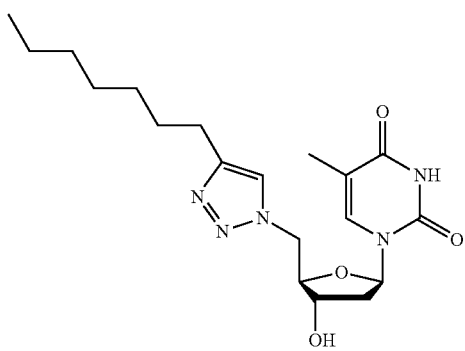

200 mg of 5'-azido-5'-deoxythymidine as described in Preparation 3 (0.75 mmol) and 93 mg of non-1-yne (1 equivalent) in a 0.1 M solution are introduced into a THF water mixture (1/1) in a flask. The following are added successively: 30 mg of sodium ascorbate (0.2 equivalent, 0.15 mmol) and 12 mg of copper sulphate (0.1 equivalent, 0.075 mmol). The reaction medium is stirred and heated at 60° C. for 5 hours. The mixture is then cooled down to ambient temperature. The reaction medium is immediately adsorbed on silica and the solvent eliminated by evaporation. The compound is obtained pure by column chromatography (AcOEt/MeOH 85/15). 120 mg of a white solid is obtained.

Rf: (AcOEt/MeOH 85/15)

The yield is 41%.

NMR $^1$H (300.13 MHz, CDCl$_3$): δ 0.83 (t, j=6 Hz, 3H, CH$_3$), δ 1.25 (m, 8H, CH$_2$), δ 1.55 (m, 2H, CH$_2$), δ 1.79 (s, 3H, CH$_3$), δ 2.10 (t, j=6 Hz, 2H, CH$_2$), δ 2.61 (t, j=6 Hz, 2H, CH$_2$), δ 4.06 (s, 1H, CH), δ 4.27 (s, 1H, CH), δ 4.59 (m, 2H, CH$_2$), δ 5.5 (s, 1H, OH), δ 6.16 (t, j=6 Hz, 1H, CH), δ 7.29 (s, 1H, CH), δ 7.82 (s, 1H, CH), δ 11.31 (s, 1H, NH).

NMR $^{13}$C (75.47 MHz, DMSO d$_6$): δ 12.6 (CH$_3$), δ 14.4 (CH$_3$), δ 22.5 (CH$_2$), δ 25.4 (CH$_2$), δ 28.9 (CH$_2$), δ 29.0 (CH$_2$), δ 29.4 (CH$_2$), δ 31.7 (CH$_2$), δ 38.4 (CH$_2$), δ 51.5 (CH$_2$), δ 71.1 (CH), δ 84.4 (CH), δ 110 (C), δ 123.1 (CH), δ 136.5 (CH), δ 147.4 (C), δ 150.9 (C=O), δ 164.1 (C=O).

EXAMPLE 8

5'-(4-(2,2-ditridecyl-[1,3]dioxolan-4-ylmethoxymethyl)-[1,2,3]triazol-1-yl)-5',2' dideoxythymidine

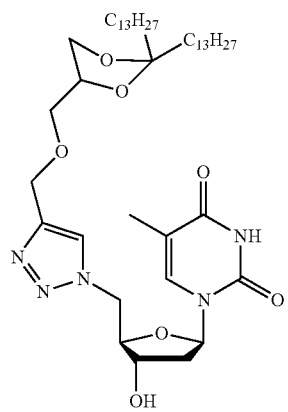

264 mg of 5'-azido-5'-deoxythymidine as described in Preparation 3 (1 mmol) and 500 mg of 4-Prop-2-ynyloxymethyl-2,2-ditridecyl-[1,3]dioxolane (1 equivalent) in a 0.1 M solution are introduced into a THF water mixture (1/1) in a flask. The following are added successively: 39.5 mg of sodium ascorbate (0.2 equivalent, 0.2 mmol) and 16 mg of copper sulphate (0.1 equivalent, 0.1 mmol). The reaction medium is stirred and heated at 60° C. for 5 hours. The mixture is then cooled down to ambient temperature. The reaction medium is then immediately adsorbed on silica and the solvent eliminated by evaporation. The compound is obtained pure by column chromatography (AcEt/MeOH 8/2). 550 mg of a white solid are obtained.

The yield is 72%.

High resolution MS [M+H]$^+$: calculated mass: 774.5745, measured mass: 774.5739

EXAMPLE 9

5'-(4-(2,2-ditridecyl-[1,3]dioxolan-4-ylbutoxymethyl)-[1,2,3]triazol-1-yl)-5',2' dideoxythymidine

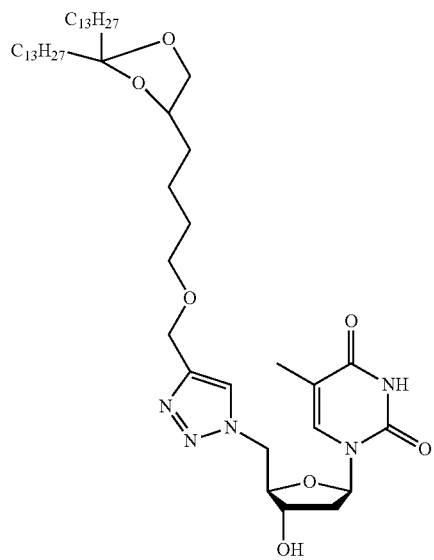

195 mg of 5'-azido-5'-deoxythymidine as described in Preparation 3 (0.73 mmol) and 400 mg of 4-(4-Prop-2-ynyloxy-butyl)-2,2-ditridecyl-[1,3]dioxolane (1 equivalent) in a 0.1 M solution are introduced into a THF water mixture (1/1) in a flask. The following are added successively: 30 mg of sodium ascorbate (0.2 equivalent, 0.15 mmol) and 12 mg of copper sulphate (0.1 equivalent, 0.073 mmol). The reaction medium is stirred and heated at 60° C. for 5 hours. The mixture is then cooled down to ambient temperature. The reaction medium is immediately adsorbed on silica and the solvent eliminated by evaporation. The compound is obtained pure by column chromatography (AcOEt/MeOH 9/1). 180 mg of a white solid is obtained.

Rf: 0.43 (AcOEt/MeOH 9/1)

The yield is 30%.

EXAMPLE 10

5'-(4-((O-cholesteryl)-methyl)-[1,2,3]triazol-1-yl)-5',2' dideoxythymidine 170 mg of 5'-azido-5'-deoxythymidine as described in Preparation 3 (0.63 mmol) and 270 mg of o-propargylcholesterol as described in Preparation 7 (1 equivalent) in a 0.1 M solution are introduced into a THF water mixture (1/1) in a flask. The following are added successively: 20 mg of sodium ascorbate (0.2 equivalent, 0.13 mmol) and 10 mg of copper sulphate (0.1 equivalent, 0.063 mmol). The reaction medium is stirred and heated at 60° C. for 5 hours. The mixture is cooled down to ambient temperature. The reaction medium is immediately adsorbed on silica and the solvent eliminated by evaporation. The compound is obtained pure by column chromatography (AcOEt/MeOH 8/2). 260 mg of a white solid is obtained.

Rf: 0.57 (AcOEt/MeOH 8/2)

The yield is 59%.

MS [M+H]$^+$: 692.3

EXAMPLE 11

1,12-bis-[5'-(4-(methyl)-[1,2,3]triazol-1-yl)-5',2' dideoxythymidine]-oxydodecane

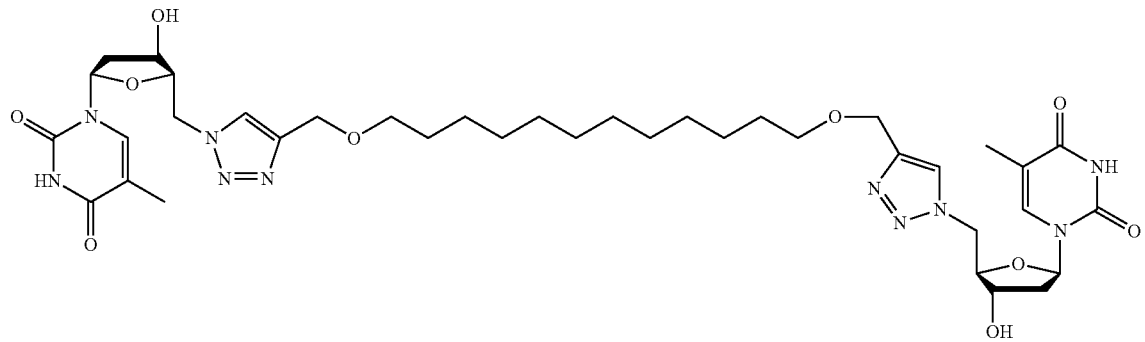

100 mg of 5'-azido-5'-deoxythymidine as described in Preparation 3 (0.375 mmol) and 52 mg of 1,12-dipropargyloxydodecane prepared from the compound described in Preparation 6 (0.5 equivalent) in a 0.1 M solution are introduced into a THF water mixture (1/1) in a flask. The following are added successively: 15 mg of sodium ascorbate (0.2 equivalent, 0.075 mmol) and 6 mg of copper sulphate (0.1 equivalent, 0.0375 mmol). The reaction medium is stirred and heated at 60° C. for 5 hours. The mixture is then cooled down to ambient temperature. The reaction medium is immediately adsorbed on silica and the solvent eliminated by evaporation. The compound is obtained pure by column chromatography (AcOEt/MeOH 8/2). 90 mg of a white solid is obtained. The yield is 59%.

NMR $^1$H (300.13 MHz, MeOH $d_4$): δ 1.28 (m, 16H, $CH_2$), δ 0.83 (m, 4H, $CH_2$), δ 1.89 (s, 6H, $CH_3$), δ 2.17 (s, 2H, $CH_2$), δ 2.25 (m, 4H, $CH_2$), δ 3.51 (t, j=6 Hz, 4H, $CH_2$), δ 4.18 (m, 2H, CH) δ 4.42 (m, 2H, OH) δ 4.58 (s, 4H, $CH_2$), δ 4.76 (qd, j=6 Hz, 4H, $CH_2$), δ 6.21 (t, j=6 Hz, 2H, CH), δ 7.23 (s, 2H, CH), δ 7.99 (s, 2H, CH).

EXAMPLE 12

5'-(4-(1(R)-hydroxy-hexyl)-[1,2,3]triazol-1-yl)-5',2' dideoxythymidine

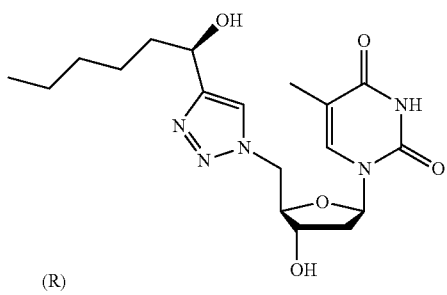
(R)

215 mg of 5'-azido-5'-deoxythymidine as described in Preparation 3 (0.8 mmol) and 101.5 mg of (R) oct-1-yn-3-ol (1 equivalent) in a 0.1 M solution are introduced into a THF water mixture (1/1) in a flask. The following are added successively: 31.5 mg of sodium ascorbate (0.2 equivalent, 0.15 mmol) and 13 mg of copper sulphate (0.1 equivalent, 0.075 mmol). The reaction medium is stirred and heated at 60° C. for 5 hours. The mixture is then cooled down to ambient temperature. The reaction medium is then immediately adsorbed on silica and the solvent eliminated by evaporation. The compound is obtained pure by column chromatography (AcEt/MeOH 9/1). 240 mg of a white solid is obtained.

Rf: 0.48 (AcEt/MeOH 9/1)

The yield is 76%.

High resolution MS [M+H]$^+$: calculated mass: 576.4125, measured mass: 576.4120

EXAMPLE 13

5'-(4-(1(S)-hydroxy-hexyl)-[1,2,3]triazol-1-yl)-5',2' dideoxythymidine

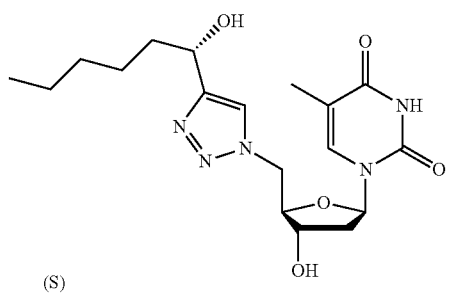
(S)

215 mg of 5'-azido-5'-deoxythymidine as described in Preparation 3 (0.8 mmol) and 101.5 mg of (S) oct-1-yn-3-ol (1 equivalent) in a 0.1 M solution are introduced into a THF water mixture (1/1) in a flask. The following are added successively: 31.5 mg of sodium ascorbate (0.2 equivalent, 0.15 mmol) and 13 mg of copper sulphate (0.1 equivalent, 0.075 mmol). The reaction medium is stirred and heated at 60° C. for 5 hours. The mixture is then cooled down to ambient temperature. The reaction medium is then immediately adsorbed on silica and the solvent eliminated by evaporation. The compound is obtained pure by column chromatography (AcOEt/MeOH 85/15). 255 mg of a white solid are obtained.

Rf: 0.48 (AcOEt/MeOH 85/15)

The yield is 78%.

High resolution MS [M+H]$^+$: calculated mass: 576.4125, measured mass: 576.4120

EXAMPLE 14

5'-(4-(1-hydroxy-hexyl)-[1,2,3]triazol-1-yl)-5',2' dideoxyadenosine

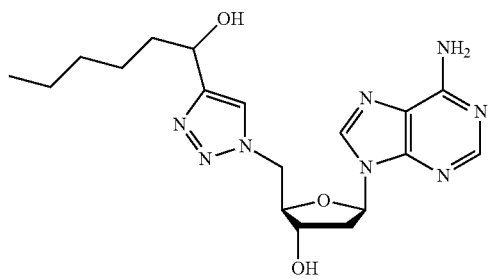

200 mg of 5'-azido-5'-deoxythymidine as described in Preparation 3 (0.75 mmol) and 95 mg of the racemic mixture of oct-1-yn-3-ol (1 equivalent) in a 0.1 M solution are introduced into a THF water mixture (1/1) in a flask. The following are added successively: 30 mg of sodium ascorbate (0.2 equivalent, 0.15 mmol) and 12 mg of copper sulphate (0.1 equivalent, 0.075 mmol). The reaction medium is stirred and heated at 60° C. for 5 hours. The mixture is then cooled down to ambient temperature. The reaction medium is immediately adsorbed on silica and the solvent eliminated by evaporation. The compound is obtained pure by column chromatography (AcOEt/MeOH 8/2). 240 mg of a white solid is obtained.

Rf: 0.47 (AcOEt/MeOH 8/2)

The yield is 80%.

High resolution MS [M+H]$^+$: calculated mass: 576.4125, measured mass: 576.4120

EXAMPLE 15

Preparation of the nanoparticles

The compound thymidine 3'-(1,2-dipalmitoyl-sn-glycero-3-phosphate) (di C16 dT) prepared in Example 2 was used as a compound of formula (I) and dioleylphosphatidylcholine (DOPC) as a co-lipid.

1) Preparation of the Stock Solutions a) Preparation of the cis-platin solution:

15 mg of cis-platin are solubilized in 10 mL of milli-Q water (5 mM). This suspension is stirred for 1 min (vortex), then incubated at 37° C. for 24 h.

b) Preparation of the lipid solutions:

Solution A: 20 mg of diC16dT are solubilized in 2 mL of chloroform (10 mg/mL). This sample is stored at −20° C.

Solution B: DOPC: solution at 20 mg/mL in chloroform, stored at −20° C.

2) Preparation of the Lipid Formulations 52.3 μL of solution A are mixed with 23.6 μL of solution B in a 2 mL Eppendorf® tube. These volumes correspond to a molar ratio of 1/1.

The chloroform is evaporated off under nitrogen in order to obtain a homogeneous lipid film.

3) Preparation of the Nanoparticles 1.2 mL of the cis-platin solution pre-incubated at 37° C. are used to rehydrate the lipid film prepared beforehand. The mixture is incubated at 37° C. for 30 min. A series of 10 heating (water bath at 45° C.) and freezing (dry ice/methanol −78° C.) cycles is carried out.

4) Washing and Recovery of the Nanoparticles

Once the series of 10 cycles is completed, the tube is centrifuged at 2100 rpm at 4° C. for 5 min. After elimination of the supernatant the pellet is re-suspended in 1 mL of milli-Q water. A second centrifugation is carried out (2100 rpm at 4° C. for 5 min), then the supernatant is removed and the pellet is dried.

The concentration (ICP/Optical) of the pellet re-suspended in 1 mL of milli-Q water is 2.844 mM equivalent in cis-platin (852.2 mg/L). This concentration corresponds to 47.4% of the cis-platin initially used.

EXAMPLE 16

Preparation of the Nanocapsules

The compound thymidine 3'-(1,2-dipalmitoyl-sn-glycero-3-phosphate) (di C16 dT) prepared in Example 2 is used as a compound of formula (I) and dioleylphosphatidylcholine (DOPC) as a co-lipid.

1) Preparation of the Stock Solutions a) Preparation of the cis-platin solution:

15 mg of cis-platin are solubilized in 10 mL of milli-Q water (5 mM). This suspension is stirred for 1 min (vortex), then incubated at 37° C. for 24 h, stirring from time to time.

b) Preparation of the lipid solutions:

Solution A: 20 mg of diC16dT are solubilized in 2 mL of dichloromethane (10 mg/mL). The solution is stored at −20° C.

Solution B: DOPC: solution at 20 mg/mL in dichloromethane, stored at −20° C.

2) Preparation of the Lipid Formulations 52.3 μL of solution A are mixed with 47.2 μL of solution B in a 2 mL Eppendorf® tube. These volumes correspond to a molar ratio of 1/1.

The dichloromethane is evaporated off with compressed nitrogen in order to obtain a homogeneous lipid film.

3) Preparation of the Nanoparticles 1.2 mL of the cis-platin solution (5 mM) are incubated overnight at ambient temperature with the lipid film prepared beforehand, without stirring. A series of 10 heating (water bath at 45° C.) and freezing (dry ice/ethanol −78° C.) cycles is carried out.

4) Washing and Recovery of the Nanoparticles

Once the series of 10 cycles is completed, the suspension is stirred and placed in a glass haemolysis tube, then subjected to sonication for 5 min. After sonication, the suspension is centrifuged at 1000 rpm/2.5 min/20° C. in order to remove the large capsules which are to be found in the pellet which will be eliminated. The supernatant is again centrifuged at 10,000 rpm/5 min/20° C. The nanoparticles are to be found in the pellet. The latter is resuspended in 1 mL of milli-Q water and a second centrifugation is carried out. The pellet is suspended in 1 mL and subjected to an Inductively Coupled Plasma (ICP) Optical assay.

EXAMPLE 17

Stability Test

The nanoparticles prepared according to the protocol of Example 16 are assayed by ICP optical spectrometry (the measured value corresponds to the total concentration). The suspension of the nanoparticles is aliquoted into 5 Eppendorf® tubes (150 μL). The latter are incubated at 37° C. under stirring (300 rpm) for different periods of time (0, 2.5, 5, 10 and 24 hours).

At a given time (x), the tube is centrifuged at 14,000 rpm/10 min/20° C. and 50 μL of supernatant (recovered carefully so as not to resuspend the pellet) are assayed.

Nanoparticles based on 1,2-dioleoyl-sn-glycero-3-[phospho-L-serine] (DOPS) with 1,2-dioleoyl-sn-glycero-3-phosphocholine (DOPC) as a co-lipid are prepared according to the same protocol as a comparison.

The percentage of release of cis-platin is calculated according to the following equation:

% of cis-platin released=$Cx-C0/Ct-C0$

Cx: concentration found at a given time (x).

C0: concentration found in the supernatant before incubation.

CT: total concentration found without incubation and without centrifugation.

The curve of the release of cis-platin as a function of the incubation time is represented in FIG. 1. The nanoparticles of Example 16 are represented by the symbol —○— and the nanoparticles based on DOPC/DOPS by the symbol —▲—

The results show that the half life (incubation time necessary to release 50% of the cis-platin) is greater than 24 h for the nanoparticles according to the invention, whereas it is of the order of 6.5 h for the nanoparticles based on DOPC/DOPS.

EXAMPLE 18

Measurement of the Size of the Nanoparticles

The nanoparticles prepared according to the protocol of Example 16 were analyzed with a MALVERN zetasizer.

The nanoparticles are suspended in 2 mL of milli-Q water (volume necessary for the size measurement). The concentration is approximately 0.5 mM (the suspension must be cloudy in order to diffuse the light). Single-use cuvettes (1 cm/1 cm) are used for the measurement.

The results show that more than 95% of the nanoparticles have a size between 100 and 250 nm with a polydispersity of 0.228.

EXAMPLE 19

Assay of Intracellular Cis-Platin

Protocol

IGROV1 cells (ovarian adenocarcinoma line) at 80% confluence (dish 10 cm in diameter) are treated with 100 µM of free cis-platin or cis-platin encapsulated in the nanoparticles of Example 16 for 2, 4 or 6 h. On completion of this treatment two washings with PBS are carried out. The cells are treated with trypsin and resuspended in PBS. Two washings of the cell suspensions with PBS are carried out (centrifugation 1000 rpm/1 min). The cells are suspended in 1 mL of PBS and counted.

ICP Optical Assay $10^6$ cells are lysed with 500 µL of the cell lysis solution (lysis buffer from SIGMA). The volume is topped up to 5 mL with milli-Q water with 1% $HNO_3$ acid.

Results

Figure 2:
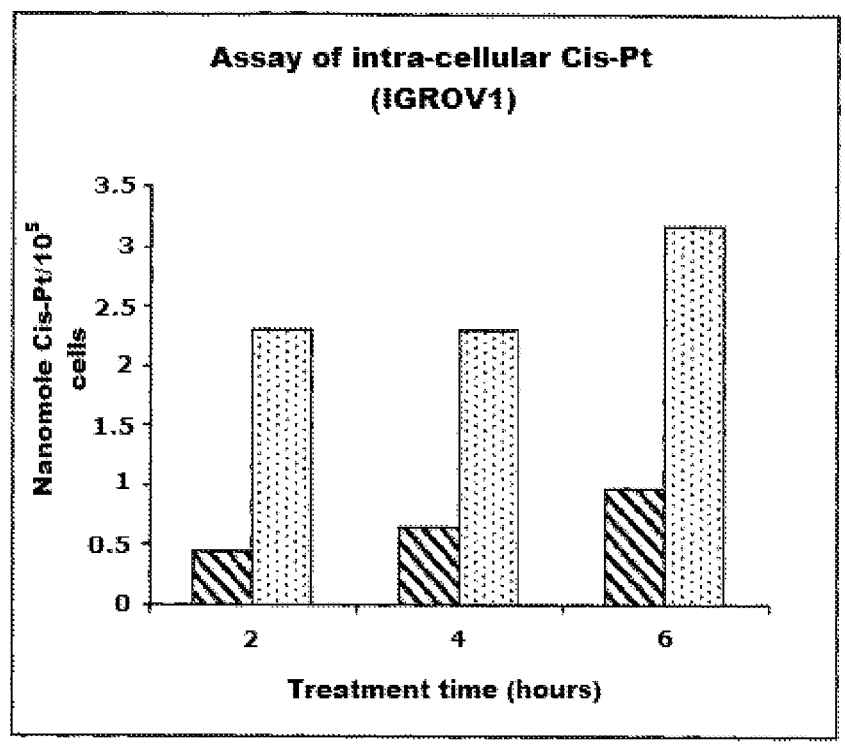
FIG. 2 is a graph showing the concentration of cis-platin released after cell lysis as a function of treatment time.

The results are represented in FIG. 2, which shows the concentration of cis-platin released after cell lysis as a function of time, corresponding to the concentration of cis-platin internalized in the treated cells.

For each period of time, the hatched column (on the left) corresponds to the free cis-platin and the dotted column (on the right) to the nanoparticles containing cis-platin.

The results show that the internalization of cis-platin is clearly more effective in the presence of the nanoparticles. For example, under identical conditions ($10^6$ cells, 100 µM, 2 h) 0.5 nanomole of cis-platin is internalized in the case of the free cis-platin whereas the internalization is 4.5 times greater in the case of the nanoparticles (2.3 nanomoles).

EXAMPLE 20

Study of the Cytotoxic Effects of the Nanoparticles Prepared According to the Invention The nanoparticles were prepared according to the process described in Example 15. Compound C20dT of formula

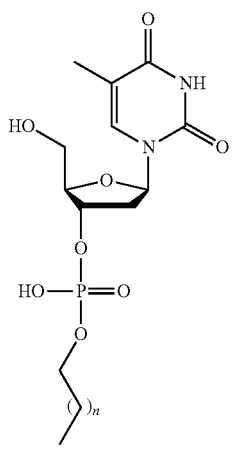

in which n=18, described in Nathalie Campins et al., New J. Chem 2007, 31, 1928-1934 is used as a compound of formula (I).

Protocol

The test implemented uses the human cancer cell line HCT8 (colorectal adenocarcinoma), known for its intrinsic resistance to platinum derivatives.

The protocol is as follows:
On D3, the cells are implanted in 96-well plates at a density of 50,000 cells per well.
On D0, the cells are treated by the formulation test, either for a short exposure period (30 min) in physiological serum, or for a long exposure period (72 h) in culture medium. The range of concentrations produced comprises the points 0-0.4-0.8-1.5-3-6.25-12.5-25-50 and 100 mg/L. Negative controls (untreated cells) and positive controls (cis-platin) were carried out simultaneously.
On D3, the culture medium is changed, and the 72 h treatment stopped.
On D6, the protocol is completed, and the cells remaining at the bottom of the well are stained with crystal violet.

Expression of the Results

The survival of the cells was determined, and the overall percentage of death (or cytotoxicity) obtained at the different test formulation concentrations was compared with that obtained with the negative controls (untreated cells). The cytotoxicity results were presented in the form of dose-effect curves characterized by their inhibitory concentration 50 ($IC_{50}$), i.e. the concentration at which 50% dead cells are observed.

Preliminary Results ($IC_{50}$) at 30 Minutes

The results are given in Table 1 below.

TABLE 1

| Compound (I) | Co-lipid | Molar ratio of the mixture | $IC_{50}$ (mg/L) |
| --- | --- | --- | --- |
| None (Cis-platin alone) | — | | Not determined $IC_{50}$ > at 100 mg/L |
| C20dT | DOPC | DOPC/C20dT 1:1 | 33 mg/L) |

The results show that the nanoparticles according to the invention, containing the compound of formula (I) C20dT, exhibit in this test, a cytotoxicity at 30 min expressed by the $IC_{50}$ at a dose significantly less than that of the cis-platin used alone.

EXAMPLE 21

Study of the Cytotoxic Effects of the Nanoparticles Prepared According to the Invention The following were used as compounds of formula (I):
diC16dT (Thymidine 3'-(1,2-dipalmitoyl-sn-glycero-3-phosphate) of Example 2 and a co-lipid (DOPC), or
5'-(4-(1(R)-hydroxy-hexyl)-[1,2,3]triazol-1-yl)-5',2' dideoxythymidine of Example 12, but without adding a co-lipid.

The nanoparticles were prepared according to the process described in Example 15, but with a single heating/cooling cycle for the compound of Example 12.

Protocol 1000 to 5000 IGROV1 cells are incubated in 100 µL of medium with serum per well (96-well plate). After 24 h the medium is removed and the cells are treated for 1 to 3 days with the formulations according to the invention and/or free cis-Pt (at the desired concentrations). The cells are incubated at 37° C. in 200 μL of medium with serum. The cell viability is revealed by an MTS colorimetric assay at the end of the treatment.

Expression of the Results

The survival of the cells was determined, and the overall percentage of death (or cytotoxicity) obtained at the different concentrations of formulations tested was compared with that obtained with the negative controls (untreated cells). The cytotoxicity results were presented in the form of dose-effect curves characterized by their inhibitory concentration 50 ($IC_{50}$), i.e. the concentration at which 50% dead cells are observed.

The results are reported in Table 2 below, in which the $IC_{50}$ is expressed either in μM, or in mg/L of cis-platin (incubation time: 24 h)

TABLE 2

| compound (I) | Co-lipid. | $IC_{50}$ Expressed in mg/L | $IC_{50}$ Expressed in μM |
|---|---|---|---|
| None (Cis-platin alone) | — | 9.48 | 31.6 |
| Example 2 | DOPC | 0.48 | 1.6 |
| Example 12 | — | 0.95 | 3.16 |

The results show that the nanoparticles according to the invention, containing the compounds of formula (I), prepared in the presence or absence of co-lipid, exhibit in this test, a cytotoxicity at 24 h expressed by the $IC_{50}$ at a dose significantly less than that of the cis-platin used alone.

EXAMPLE 22

Figure 3:
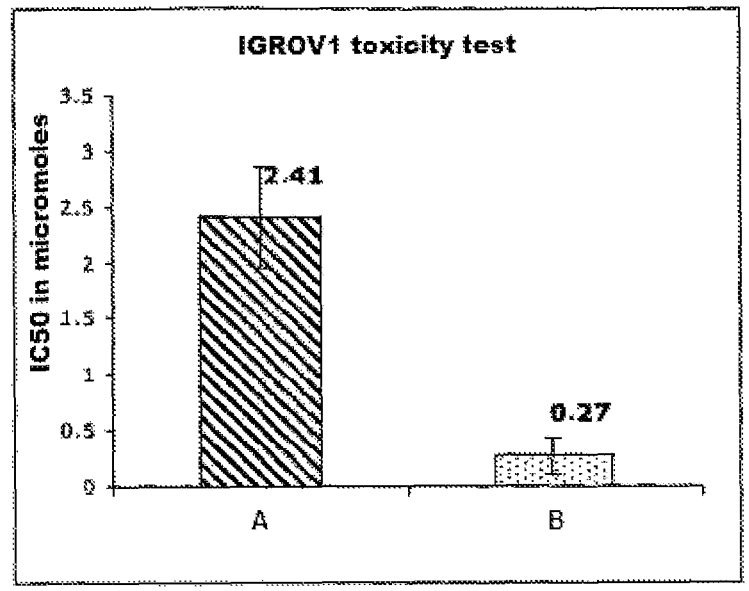
FIGS. 3A and 3B are graphs showing the concentration necessary to obtain 50% cell death (IC50) with free cis-platin (A) or the nanoparticles containing cis-platin (B) for the IGROV1 (FIG. 3A) and SKOV3 (FIG. 3B) cell lines.
Figure 3:
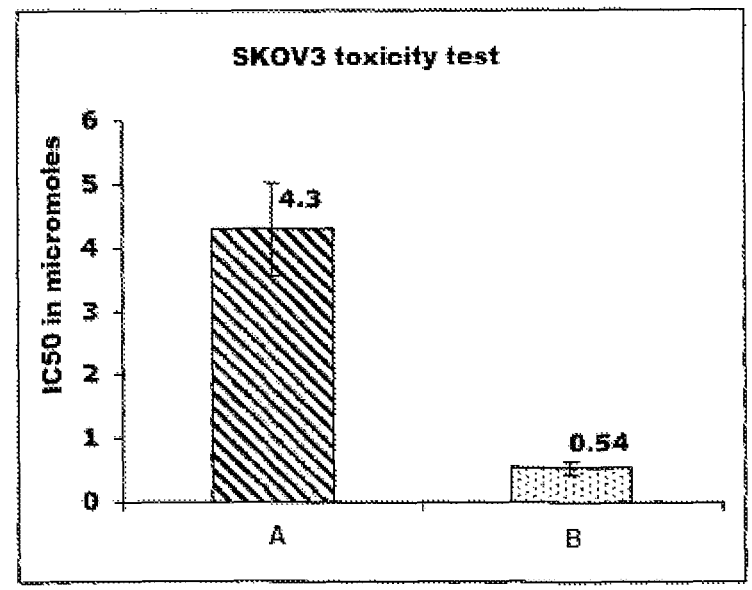

Study of the Cytotoxic Effects of the Nanoparticles Prepared According to the Invention Protocol a/ Preparation and Treatment of the Cells:

2500 cells (IGROV1, SKOV3, ovarian adenocarcinoma lines) per well are incubated in 100 μL of the medium with serum in a 96-well plate. After 24 hours the medium is aspirated and the cells are treated with free cis-platin or cis-platin encapsulated in the nanoparticles of Example 16 in 100 μL of the medium without serum at different concentrations (500, 100, 10, 1, 0.1, 0.01, 0.001 μM). After treatment for 24 hours, the medium is removed and the cells are washed twice with 100 μL of PBS then incubated with 100 μL of the medium with serum.

b/ Revelation of the Toxicity:

48 hours after the two washings, the cell viability is revealed by adding 20 μL of MTS. The absorbance at 490 nm is measured after incubation for 2 to 4 hours at 37° C. The absorbance is proportional to the cell viability.

c) Results:

The results are represented in FIG. 3, which shows the concentration necessary to obtain 50% cell death (IC50) with free cis-platin (column A) or the nanoparticles containing cis-platin (column B).

FIG. 3A relates to the cell line IGROV1 and FIG. 3B relates to the cell line SKOV3.

The results show that the nanoparticles of Example 16 containing cis-platin are more effective than the free cis-platin in the two cell lines, IGROV1 (sensitive to cis-platin) and SKOV3 (resistant to cis-platin).

On the line IGROV1, 50% cell death is obtained with 0.27 μM of nanoparticles containing cis-platin whereas it is necessary to use 2.41 μM of free cis-platin in order to obtain this result. On the line SKOV3, 50% cell death is obtained with 0.54 μM of nanoparticles containing cis-platin as against 4.3 μM of free cis-platin.

The nanoparticles containing cis-platin are respectively 9 and 8 times more effective than the free cis-platin on the lines IGROV1 and SKOV3.

The invention claimed is:

1. A process for encapsulating a therapeutic agent comprising the steps of:
   a) preparing a mixture of a therapeutic agent and at least one functional amphiphilic compound of formula (I)

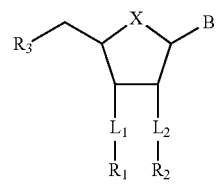

wherein
   X is an oxygen atom,
   B is a purine base or a pyrimidine base,
   $L_1$ and $L_2$, identical or different, are hydrogen or a hydroxyl group, provided that $L_1$ and $L_2$ are not simultaneously a hydroxyl group,
   $R_1$ and $R_2$ do not exist, and
   $R_3$ is a triazole group, wherein the triazole group is unsubstituted or substituted by $C_2$-$C_{30}$ alkyl or $(CH_2)_m$—O—$(CH_2)_p$—$R_9$, wherein m is from 1 to 6, p is from 0 to 10, and $R_9$ is a cyclic ketal group containing from 5 to 7 atoms, and wherein the cyclic ketal group is unsubstituted or substituted by a sterol radical or at least one selected from the group consisting of linear $C_2$-$C_{30}$ alkyl and branched $C_2$-$C_{30}$ alkyl;
   b) subjecting said mixture to repeated heating and freezing cycles to obtain nanoparticles containing said therapeutic agent; and
   c) recovering the nanoparticles containing said therapeutic agent.

2. The process according to claim 1, wherein B is thymine or adenine.

3. The process according to claim 1, wherein in formula (I):
   $L_1$ is a hydroxyl group, $L_2$ is hydrogen, and $R_3$ is a triazole group substituted by a $C_2$-$C_{30}$ alkyl chain optionally substituted by a hydroxyl group; or
   $L_1$ is a hydroxyl group, $L_2$ is hydrogen, and $R_3$ is a triazole group substituted by $(CH_2)_m$—O—$(CH_2)_p$—$R_9$, wherein m is from 1 to 6, p is from 0 to 10, and $R_9$ is a cyclic ketal group containing from 5 to 7 atoms, and wherein the cyclic ketal group is unsubstituted or substituted by a sterol radical or at least one selected from the group consisting of linear $C_2$-$C_{30}$ alkyl and branched $C_2$-$C_{30}$ alkyl.

4. The process according to claim 1, comprising the steps of:
   putting the compound of formula (I) in solution in an organic solvent to form a lipid mixture,
   evaporating the organic solvent from the lipid mixture to form a lipid film, putting the therapeutic agent in distilled water at a concentration of 0.1 ng/mL to 10 mg/mL to form a therapeutic agent solution, combining the lipid film with the therapeutic agent solution to form a rehydrated lipid film, and subjecting the rehydrated lipid film to 1 to 10 cycles of heating and cooling.

5. The process according to claim 1, further comprising the step of putting the compound of formula (I) in solution in an organic solvent in the presence of a co-lipid.

6. The process according to claim 1, further comprising the step of putting the compound of formula (I) in solution in an organic solvent in the presence of a co-lipid, wherein the co-lipid is chosen from dioleylphosphatidylcholine (DOPC) and dioleyl phosphatidyluridinephosphatidylcholine (DOUPC).

7. The process according to claim 1, wherein B is uracil, adenine, guanine, cytosine, thymine, or hypoxanthine.

8. The process according to claim 1, wherein in formula (I):
 X is an oxygen atom,
 B is thymine,
 $L_1$ is a hydroxyl group,
 $L_2$ is hydrogen, and
 $R_3$ is a triazole group substituted by $C_6$ alkyl, $C_7$ alkyl, or $(CH_2)_m$—O—$(CH_2)_p$—$R_9$, wherein in $(CH_2)_m$—O—$(CH_2)_p$—$R_9$
 m is 1, p is 1, and $R_9$ is a ketal group disubstituted by a $C_{13}H_{27}$ group;
 m is 1, p is 4, and $R_9$ is a ketal group disubstituted by a $C_{13}H_{27}$ group; or
 m is 1, p is 0, and $R_9$ is a sterol radical.

9. The process of claim 1, wherein the compound of formula (I) is selected from the group consisting of:
 5'-(4-(1-hydroxy-hexyl)-[1,2,3]triazol-1-yl)-5',2'dideoxythymidine,
 5'-(4-(hexyl)-[1,2,3]triazol-1-yl)-5',2'dideoxythymidine,
 5'-(4-(heptyl)-[1,2,3]triazol-1-yl)-5',2'dideoxythymidine,
 5'-(4-(2,2-ditridecyl-[1,3]dioxolan-4-ylmethoxymethyl)-[1,2,3]triazol-1-yl)-5',2'dideoxythymidine,
 5'-(4-(2,2-ditridecyl-[1,3]dioxolan-4-ylbutoxymethyl)-[1,2,3]triazol-1-yl)-5',2'dideoxythymidine,
 5'-(4-((O-cholesteryl)-methyl)-[1,2,3]triazol-1-yl)-5',2'dideoxythymidine,
 5'-(4-(1(R)-hydroxy-hexyl)-[1,2,3]triazol-1-yl)-5',2'dideoxythymidine,
 5'-(4-(1(S)-hydroxy-hexyl)-[1,2,3]triazol-1-yl)-5',2'dideoxythymidine, and
 5'-(4-(1-hydroxy-hexyl)-[1,2,3]triazol-1-yl)-5',2'dideoxyadenosine.

* * * * *

UNITED STATES PATENT AND TRADEMARK OFFICE
CERTIFICATE OF CORRECTION

PATENT NO. : 9,533,049 B2  
APPLICATION NO. : 14/208978  
DATED : January 3, 2017  
INVENTOR(S) : Barthelemy et al.

Page 1 of 1

It is certified that error appears in the above-identified patent and that said Letters Patent is hereby corrected as shown below:

On the Title Page

Item (71) Applicants, the third listed applicant "UNIVERSITE DE LA MEDITERRANEE" should read as follows:

--UNIVERSITE DE LA MEDITERRANEE, Marseille (FR)--.

Item (72) Inventors, the second listed inventor "Michel Camplo" should read as follows:

--Michel Camplo, Marseille (FR)--.

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*